United States Patent [19]

Diethelm

[11] 4,277,399

[45] Jul. 7, 1981

[54] PROCESS FOR PREPARING PYRENZEPINE

[75] Inventor: Eugen Diethelm, Triesen, Liechtenstein

[73] Assignee: Grissman Chemicals Limited, London, England

[21] Appl. No.: 157,099

[22] Filed: Jun. 6, 1980

[30] Foreign Application Priority Data

Jul. 9, 1979 [GB] United Kingdom ............... 23884/79

[51] Int. Cl.$^3$ ............................................ C07D 487/04
[52] U.S. Cl. ............................................ 260/239.3 T
[58] Field of Search ................................ 260/239.3 T

[56] References Cited

U.S. PATENT DOCUMENTS

| | | | |
|---|---|---|---|
| 3,406,168 | 10/1968 | Schmidt ........................ | 260/239.3 T |
| 3,539,554 | 11/1970 | Schmidt et al. ............... | 260/239.3 T |
| 3,660,380 | 5/1972 | Schmidt et al. ............... | 260/239.3 T |
| 4,210,648 | 7/1980 | Schmidt et al. ............... | 260/239.3 T |
| 4,213,984 | 7/1980 | Schmidt et al. ............... | 260/239.3 T |
| 4,213,985 | 7/1980 | Schmidt et al. ............... | 260/239.3 T |

*Primary Examiner*—Robert T. Bond
*Attorney, Agent, or Firm*—Ostrolenk, Faber, Gerb & Soffen

[57] ABSTRACT

Pyrenzepine, as such or as an acid addition salt, is made by reacting a lower alkyl ester of o-aminobenzoic acid with 3-aminopyridine in the presence of a base and reacting the tricyclic product with a mixed anhydride of methyl-piperazine acetic acid.

5 Claims, No Drawings

PROCESS FOR PREPARING PYRENZEPINE

DESCRIPTION

The present invention relates to the preparation of pyrenzepine as the base or as an acid addition salt such as the dihydrochloride.

Pyrenzepine has a very useful anti-ulcer activity. It is usually prepared from o-nitrobenzoic acid, which is transformed into the acid chloride and then amidated with 3-amino-pyridine. The nitro group is then reduced and the amino group is bonded to the pyridine ring in the 2-position. Subsequently the side chain is attached to the amino group in two steps.

According to the present invention, pyrenzepine having the formula:

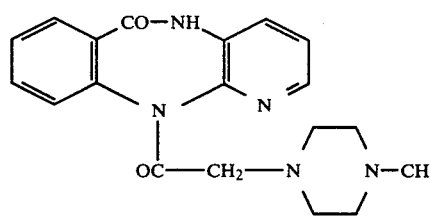
(I)

or an acid addition salt thereof is prepared by (1) reacting a lower alkyl (preferably methyl) ester of o-aminobenzoic acid with 3-aminopyridine in the presence of a base (preferably sodium amide) to produce a tricyclic compound of formula:

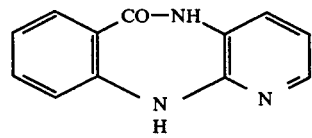
II and (2) reacting the said tricyclic compound with a mixed anhydride of N-methyl-piperazine acetic acid of the formula:

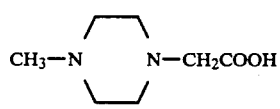
III (preferably that obtained with ethyl chloroformate) to produce pyrenzepine which is isolated as such or as an acid addition salt thereof.

The tricyclic compound is preferably prepared by reacting 1 mole of the methyl ester of o-amino-benzoic acid (which is easily available) in dimethylsulphoxide, in the presence of sodium methylate or preferably sodium-amide, and at a temperature between 60°–80° C. with 1 mole of 3-aminopyridine. After cooling, the reaction mixture is neutralized cautiously with hydrochloric acid, the reaction mixture is concentrated in vacuo and the product is extracted with a non-water-soluble solvent. It is advisable to use the same solvent as that used for preparing the mixed anhydride so that the compound does not need to be separated. The yield of the tricyclic compound is not less than 70% of the theoretical.

N-methyl-piperazine acetic acid is easily prepared by reacting N-methyl-piperazine with monochloro-acetic acid. The mixed anhydride of this acid can be prepared in an anhydrous, inert solvent, at a temperature between 0° and 5° C., by reacting 1 mole of the acid with 1 mole of ethyl-chloroformate in the presence of 1 mole of triethylamine. After filtering off the hydrochloride, the mixed anhydride obtained is reacted with the secondary amino group of the tricyclic compound. The yield of this reaction is greater than 90% of the theoretical.

The following Example illustrates the invention.

EXAMPLE

Preparation of the tricyclic compound 15.1 g of the methyl ester of o-aminobenzoic acid are added to 200 ml of dimethylsulphoxide. Then 9.4 g of 3-aminopyridine and 5.4 g of sodium-amide are added thereto. The temperature is raised to 70° C. and the reaction mixture is stirred for 3 hours.

After cooling, the pH is cautiously adjusted to 7 with dilute hydrochloric acid and the reaction mixture is then concentrated in vacuo to one-fourth of the initial volume. The concentrated reaction mixture is extracted with ether to give an ether solution of the desired compound in a yield of 70%.

Preparation of pyrenzepine dihydrochloride

To a benzene solution of 0.1 mole of the mixed anhydride of N-methyl-piperazine acetic acid, an ether solution of 1 mole of the tricyclic compound is added at a temperature between 0° and 5° C. Carbon dioxide is liberated. After evaporation of one-third of the solvent, the reaction mixture is saturated with hydrogen chloride. The desired compound is thus precipitated in a yield greater than 90%, m.p. 255°–260° C. (dec.). The I.R. and U.V. spectra confirm the structure of the product.

I claim:

1. A process for the preparation of pyrenzepine having the formula:

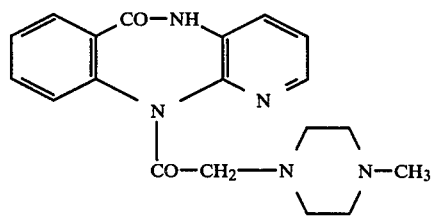

or an acid addition salt thereof which comprises (1) reacting a lower alkyl ester of o-aminobenzoic acid with 3-aminopyridine in the presence of a base to produce a tricyclic compound of formula:

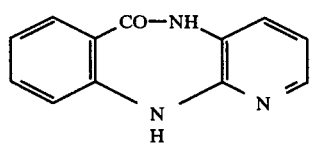

and (2) reacting the said tricyclic compound with a mixed anhydride of N-methyl-piperazine acetic acid of the formula:

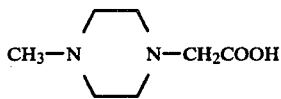

to produce pyrenzepine which is isolated as such or as an acid addition salt thereof.

2. Process according to claim 1 in which the methyl ester of o-aminobenzoic acid is reacted with 3-aminopyridine in the presence of sodium amide.

3. Process according to claim 4 in which the pyrenzepine is isolated as the dihydrochloride.

4. Process according to claim 1, 2 or 4 in which the said mixed anhydride used has been produced by the reaction of N-methyl-piperazine acetic acid with ethyl chloroformate.

5. Process according to claim 3, in which the said mixed anhydride used has been produced by the reaction of N-methyl-piperazine acetic acid with ethyl chloroformate.

* * * * *

Disclaimer 4,277,399.—*Eugen Diethelm*, Triesen, Liechtenstein. PROCESS FOR PREPARING PYRENZEPINE. Patent dated July 7, 1981. Disclaimer filed Mar. 23, 1982, by the assignee, *Grissman Chemicals Ltd.*

Hereby enters this disclaimer to all claims of said patent.

[*Official Gazette October 5, 1982.*]